United States Patent
Omori et al.

(10) Patent No.: US 8,965,712 B2
(45) Date of Patent: Feb. 24, 2015

(54) LIFE PREDICTING METHOD FOR SOLDER JOINT, LIFE PREDICTING APPARATUS FOR SOLDER JOINT AND ELECTRONIC DEVICE

(75) Inventors: Takahiro Omori, Kanagawa-ken (JP); Kenji Hirohata, Tokyo (JP); Tomoko Monda, Kanagawa-ken (JP); Katsuaki Hiraoka, Kanagawa-ken (JP); Minoru Mukai, Tokyo (JP)

(73) Assignee: Kabushiki Kaisha Toshiba, Tokyo (JP)

(*) Notice: Subject to any disclaimer, the term of this patent is extended or adjusted under 35 U.S.C. 154(b) by 1013 days.

(21) Appl. No.: 13/051,881

(22) Filed: Mar. 18, 2011

(65) Prior Publication Data
US 2012/0072129 A1    Mar. 22, 2012

(30) Foreign Application Priority Data
Sep. 16, 2010   (JP) ................. P2010-208553

(51) Int. Cl.
*G01B 3/44* (2006.01)
*B23K 31/12* (2006.01)
(Continued)

(52) U.S. Cl.
CPC .......... *B23K 31/125* (2013.01); *B23K 1/00* (2013.01); *H01L 24/17* (2013.01); *G01N 2203/0073* (2013.01); *G01N 2203/0212* (2013.01); *G01R 31/048* (2013.01); *H05K 1/0271* (2013.01); *H05K 3/3436* (2013.01); *H01L 2224/17517* (2013.01); *H01L 24/13* (2013.01);
(Continued)

(58) Field of Classification Search
CPC ..... G01R 31/048; G06F 17/00; G01N 27/045

USPC ........................................... 702/34
See application file for complete search history.

(56) References Cited

U.S. PATENT DOCUMENTS

| 5,867,809 A | 2/1999 | Soga et al. |
| 7,467,076 B2 | 12/2008 | Sakai |

(Continued)

FOREIGN PATENT DOCUMENTS

| JP | 3-128431 | 5/1991 |
| JP | 3012948 | 4/1995 |

(Continued)

OTHER PUBLICATIONS

Notification of Reasons for Refusal issued by the Japanese Patent Office on Aug. 28, 2012, for Japanese Patent Application No. 2010-208553, and English-language translation thereof.

(Continued)

*Primary Examiner* — Phuong Huynh
(74) *Attorney, Agent, or Firm* — Finnegan, Henderson, Farabow, Garrett & Dunner, L.L.P.

(57) ABSTRACT

A life predicting method for a solder joint includes a step of referring to a temperature history of a measurement object having a solder joint, a step of examining at least one physical quantity selected from the group consisting of amplitude, a cycle number, a mean temperature, and a periodic length of a temperature variation with a cycle count method from the temperature history, a step of calculating a strain range by utilizing a previously prepared response surface from the physical quantity examined with the cycle count method, and a step of calculating a strain range increasing rate from a strain range with reference to a previously obtained damage index and a strain variation history of the strain range.

10 Claims, 14 Drawing Sheets

(51) Int. Cl.
  *B23K 1/00*      (2006.01)
  *H01L 23/00*     (2006.01)
  *G06F 11/30*     (2006.01)
  *G01R 31/04*     (2006.01)
  *H05K 1/02*      (2006.01)
  *H05K 3/34*      (2006.01)

(52) U.S. Cl.
  CPC .......... *H01L 24/14* (2013.01); *H01L 2224/131* (2013.01); *H01L 2224/14517* (2013.01); *H01L 2224/16225* (2013.01); *H01L 2924/1432* (2013.01); *H01L 2924/1434* (2013.01); *H01L 2924/3011* (2013.01); *H01L 2924/10253* (2013.01)
  USPC .............. 702/34; 702/182; 702/183; 702/184

(56) References Cited

U.S. PATENT DOCUMENTS

| | | |
|---|---|---|
| 8,222,737 B2 | 7/2012 | Watanabe et al. |
| 2010/0070204 A1* | 3/2010 | Monda et al. .................... 702/35 |
| 2010/0250149 A1 | 9/2010 | Omori et al. |
| 2012/0072129 A1* | 3/2012 | Omori et al. .................... 702/34 |
| 2012/0179391 A1 | 7/2012 | Omori et al. |

FOREIGN PATENT DOCUMENTS

| | | |
|---|---|---|
| JP | 7-306239 | 11/1995 |
| JP | 8-70062 | 3/1996 |
| JP | 3012948 | 2/2000 |
| JP | 2004-79914 | 3/2004 |
| JP | 2004-85397 | 3/2004 |
| JP | 2005-26250 | 1/2005 |
| JP | 2005-109084 | 4/2005 |
| JP | 2005-310837 | 11/2005 |
| JP | 2006-84248 | 3/2006 |
| JP | 2006-313127 | 11/2006 |
| JP | 3900042 | 4/2007 |
| JP | 2008-2869 | 1/2008 |
| JP | 2009-218390 | 9/2009 |
| JP | 2010-73795 | 4/2010 |
| JP | 2010-223859 | 10/2010 |
| JP | 4648505 | 3/2011 |
| WO | WO 2005/088483 A1 | 9/2005 |
| WO | WO 2011/036751 A1 | 3/2011 |
| WO | WO 2011/121725 A1 | 10/2011 |

OTHER PUBLICATIONS

Mukai et al., "Damage Path Simulation of Solder Bumps Under Mechanical Fatigue Tests," Japan Society of Mechanical Engineers (Dec. 2007),73:115-121.

* cited by examiner

US 8,965,712 B2

LIFE PREDICTING METHOD FOR SOLDER JOINT, LIFE PREDICTING APPARATUS FOR SOLDER JOINT AND ELECTRONIC DEVICE

CROSS REFERENCE TO RELATED APPLICATION

This application is based upon and claims the benefit of priority from the prior Japanese Patent Application No. 2010-208553, filed on Sep. 16, 2010, the entire contents of which are incorporated herein by reference.

FIELD

Embodiments relate basically to a life predicting method for a solder joint, a life predicting apparatus for a solder joint and an electronic device.

BACKGROUND

There exist various kinds of malfunctions of electronic devices under usage conditions thereof. Above all, a malfunction of a joint portion such as a solder joint is particularly one of troublesome defect phenomena which occur frequently. Once such a malfunction occurs, the malfunction causes a serious influence to device operation. Even a small strain fracturing nothing at one time could accumulate at a solder joint as a result of repetition of various loads, e.g., thermal loads due to power ON/OFF or external mechanical loads, thereby causing metallic fatigue at the solder joint. There is known a structural health monitoring technology of an electronic device to predict a life of the electronic device until the electronic device breaks down because of solder joint trouble due to such a fatigue phenomenon.

In order to accurately predict a metallic fatigue life for solder joints or other parts metals, it is important to accurately estimate an amount of strain occurring at a point to be estimated. However, in most cases, variations in the strain involved in a damage progression such as a crack progression at a solder joint are not estimated in the life prediction of a BGA (Ball Grid Array) solder joint. The variations in the strain amount involved in the crack progression at the solder joint are not taken into consideration for the life prediction of the BGA solder joint. That is, in most cases, a strain estimation is carried out as is for an initial damage progression at a solder joint even for the damage progression subsequent to the initial one, i.e., even after the strain amount becomes large as a result of a decrease in stiffness at the solder joint. Here is a time-consuming job to prepare a damage model (i.e., a model to estimate damage indexes of a solder joint on the basis of a temperature change) and simpler algorithm for implementation. When such a time-consuming job is taken into consideration, a method without involving the time-consuming job may provide a practical prediction even though the life prediction accuracy thereof lowers. However, under normal conditions, strain amplitude accumulated at the solder joint promotes cracks in the solder to decrease stiffness of the solder joint. Therefore, a rate of stress to be received by each solder joint varies in accordance with temperature change. Accordingly, a life of a signal bump at an inner location which is predicted from a dummy bump at an outer location is to cause an error against an actual life unless progression of damage is considered. Here, the error of life is mainly caused by a difference between estimated strain and actual strain of each bump due to stiffness variations.

BRIEF DESCRIPTION OF DRAWINGS

Aspects of this disclosure will become apparent upon reading the following detailed description and upon reference to the accompanying drawings. The description and the associated drawings are provided to illustrate embodiments of the invention and not limited to the scope of the invention.

DESCRIPTION

Figure 1:
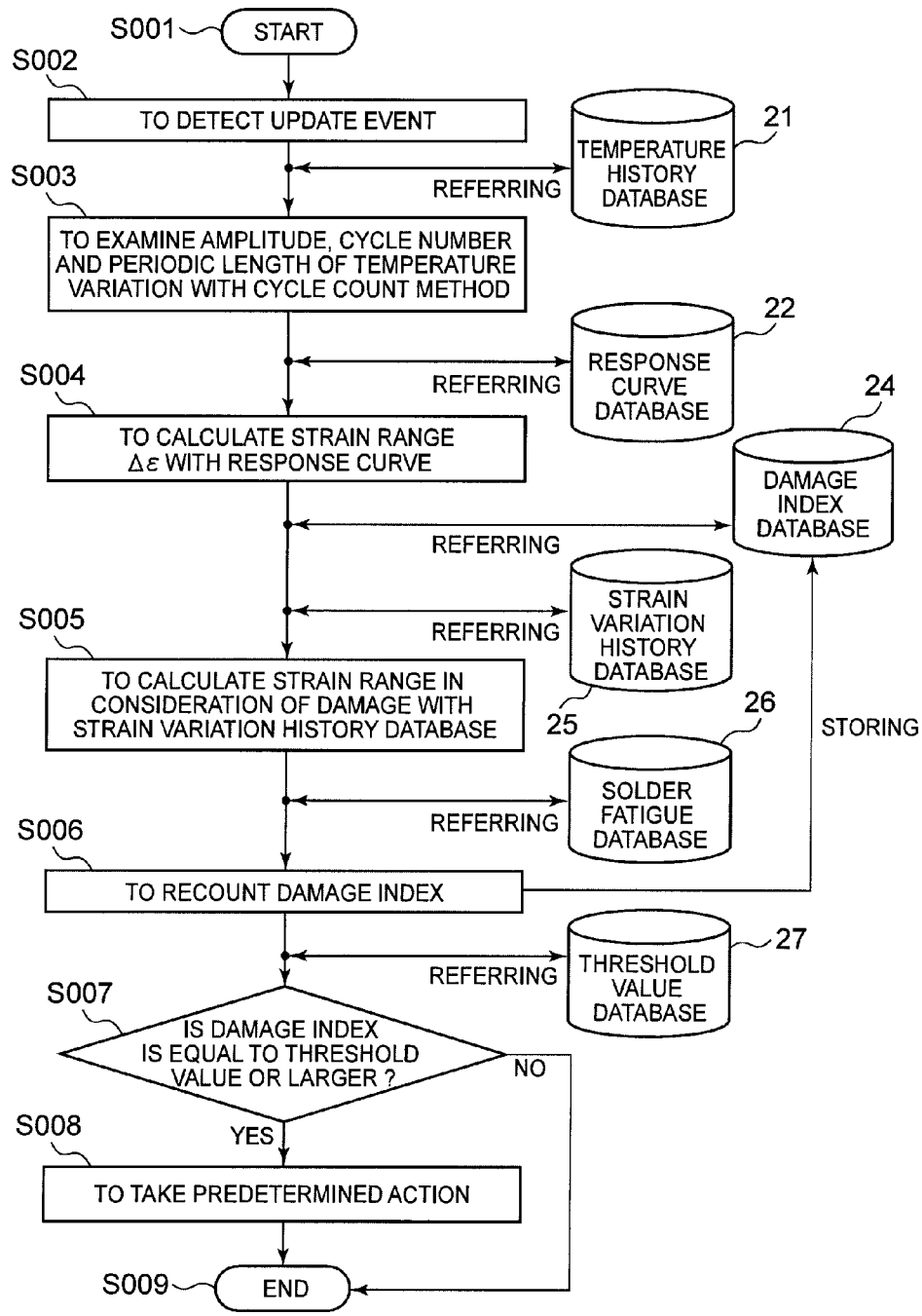
FIG. 1 is a flowchart of a process according to a first embodiment.

As will be described below, according to an embodiment, a life predicting method for a solder joint includes a step of referring to a temperature history of a measurement object having a solder joint, a step of examining at least one physical quantity selected from the group consisting of amplitude, a cycle number, a mean temperature, and a periodic length of a temperature variation with a cycle count method from the temperature history, a step of calculating a strain range by utilizing a previously prepared response surface from the physical quantity examined with the cycle count method, and a step of calculating a strain range increasing rate from the strain range with reference to a previously obtained damage index and a strain variation history of the strain range.

According to another embodiment, a life predicting apparatus for a solder joint includes a first memory, a second memory unit, a third memory, a fourth memory, a first control unit, a second control unit, a third control unit, and a fourth control unit. The first memory stores a temperature history of a measurement object having a solder joint. The second memory stores a response surface for obtaining a strain range from at least one physical quantity of amplitude, a cycle number, a mean temperature, and a periodic length of temperature variations. The third memory stores a history of a damage index. The fourth memory stores strain variations for obtaining a strain range increasing rate from a damage index. The first control unit obtains the temperature history with reference to the first memory unit. The second control unit examines at least one physical quantity selected from the group consisting of amplitude, a cycle number, a mean temperature, and a periodic length of temperature variations with a cycle count method from the history information of temperature. The third control unit calculates a strain range from the physical quantity examined with a cycle count with reference to the second memory unit. The fourth control unit calculates the strain range increasing rate from the strain range calculated by the third control unit with reference to the third memory unit and the fourth memory unit.

According to another embodiment, an electronic device includes an electronic component, a mounting board, a first joint, a second joint, and a third joint. The first joint mechanically connects the electronic component and the mounting board and mediates an exchange of an electric signal between the electronic component and the mounting board. The second joint mechanically connects the electronic component and the mounting board and not to mediate the exchange of the electric signal between the electronic component and the mounting board. The third joint formed between the first joint and the second joint mechanically connects the electronic component and the mounting board and monitors a connection state between the electronic component and the mounting board.

Embodiments will be described below with reference to the drawings.

First Embodiment

As a first embodiment, a predicting method of a solder life will be explained with reference to FIGS. 1 and 2.

(Steps S001 to S002)

A first control unit (i.e., an update event detection unit) 11 detects an event of life updating to refer to a second memory unit (i.e., a temperature history database) 22 for temperature information stored by the time of the updating.

An instruction program to trigger the event of life updating at regular time intervals is stored in firmware stored in a first memory unit (i.e., an update event storage unit) 21, and the update event detection unit 11 executes the program to enable the event of life updating.

A history of previous temperatures is stored in the temperature history database 22. The temperature of a board 1 is measured by a detection unit 7 and is stored in the temperature history database 22.

(Step S003)

A second control unit (i.e. a cycle count examination unit) 12 examines information such as temperature amplitude, a cycle number, a mean temperature and a periodic length with a cycle count method to be mentioned below, with reference to the temperature history database 22.

The temperature history database 22 stores a temperature measured by the detection unit 7 and time at which the temperature is measured as time-series data.

(Step S004)

A third control unit (i.e., a temperature-amplitude/strain-range conversion unit) 13 converts temperature amplitude $\Delta T$ into a strain range $\Delta \epsilon$ on the basis of the information including temperature amplitude, a cycle number, a mean temperature and a periodic length obtained by the cycle count examination unit 12 with reference to a response surface stored in a third memory unit (i.e., a response surface database) 23.

The response surface database 23 stores the response surface which is a function of amplitude, a cycle number, mean temperature and periodic length of temperature variation and a strain range. The strain range can be obtained from the amplitude, the cycle number, the mean temperature and the periodic length of the temperature variation by utilizing the response surface. The response surface is previously stored in the third memory unit (i.e., the response surface database) 23.

(Step 005)

A fourth control unit (i.e., a strain-range increasing rate calculation unit) 14 calculates an increasing rate of a strain range (referred to as strain-range increasing rate below) occurring as a result of a progression of damage accumulated at a solder joint 71 at the time when an event is currently updated by utilizing the converted strain range $\Delta \epsilon$ with reference to a fourth memory unit (i.e., a damage index database) 24 and a fifth memory unit (i.e., a strain variation history database) 25.

The damage index database 24 stores a damage index and time at which the damage index is obtained as time-series data. The strain variation history database 25 stores a function of the damage index and a strain-range increasing rate.

For example, after a damage index D1 is obtained at certain time t1 from the damage index database 24, a strain-range increasing rate $\alpha$ can be obtained from the damage index D1. Then, for example, a new strain range $\Delta \epsilon 2 = \alpha \cdot \Delta \epsilon 1$ can be obtained from the strain range $\Delta \epsilon 1$ by utilizing the strain-range increasing rate $\alpha$.

(Step S006)

A fifth control unit (i.e., a strain-range recount unit) 15 recounts a damage index with considering the strain range increasing rate calculated at S005. Then, the newly obtained damage index is stored in the fourth memory unit (the damage index database) 24 with the time at which the current event is updated.

In the above example, a damage index D2 can be newly obtained from the newly obtained strain range $\Delta \epsilon 2$ by utilizing the equation 1 and the equation 2 both to be mentioned later. The newly obtained damage index D2 is stored in the damage index database 24 along with the time t2 thereof.

(Step S007)

A sixth control unit (i.e., a damage index determination unit) 16 determines whether or not the new damage index is equal to a specific threshold value or larger with reference to a seventh memory unit (i.e., a threshold value database) 27. When the new damage index is equal to the specific threshold value or larger, the damage index determination unit 16 is allowed to transmit an instruction signal to take a predetermined action.

Examples of the predetermined action include automatically taking backups of data on the assumption that a malfunction is coming, informing a user of a possibility of a malfunction, informing a server managing devices that the devices have little time left to perform, or the like.

The specific threshold value can be appropriately set in accordance with a product type, a product usage or the like. For example, the threshold value may be strictly set for an electric power plant or medical equipment which require high reliability. In contrast, the threshold value may be loosely set for a server of a network system having a backup mechanism in case of failure.

(Operation, Function and Technical Significance)

Here, a mounting board having solder joints is assumed as a product to be a measurement object. The technical significance of the first embodiment will be further explained with reference to a method of predicting a fatigue life of a ball grid array (BGA), the method aiming at thermally-varied loads under actual usage conditions after the product is shipped.

The first embodiment is characterized by predicting the lives of solder joints on the basis of decreases in stiffness due to damage of the respective solder joints.

Figure 4:
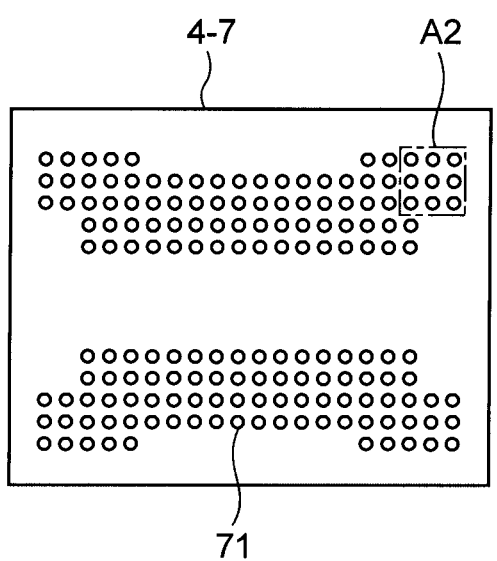
FIG. 4 is an enlarged view of a solder joint of an area of A1 in FIG. 3.
Figure 5:
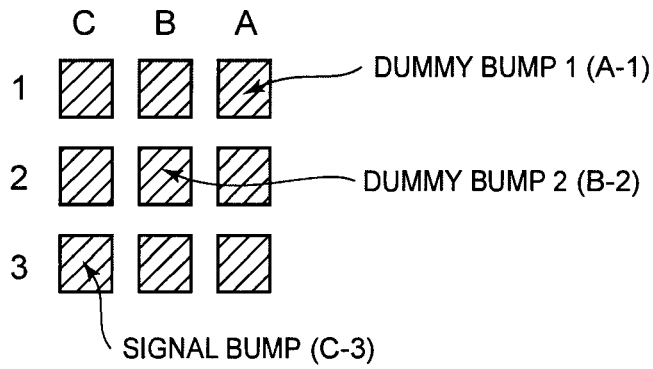
FIG. 5 is an enlarged view of a solder joint of an area of A2 in FIG. 4.
Figure 6:
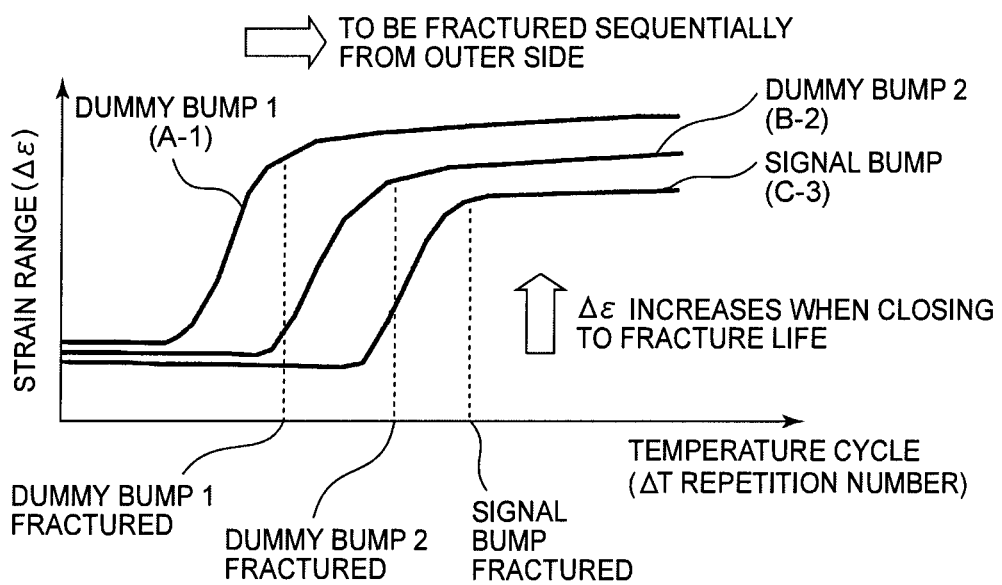
FIG. 6 is a conceptual graph showing relation among a position of a solder joint, a temperature cycle and a strain range.

FIG. 6 is a schematic graph showing a damage progression of a solder joint. FIG. 6 schematically shows variation of strain ranges caused by the damage progression when a BGA receives a temperature cyclic load for a dummy bump 1 (A-1), a dummy bump 2 (B-2) and a signal bump 3 (C-3) of solder joints shown in FIG. 5. Here, the dummy bump 1, the dummy bump 2 and the signal bump 3 are included in an area A2 surrounded by a dashed-dotted line at the upper right corner of a component 4-7 shown in FIG. 4. The area A2 shown in FIG. 4 is a detailed view showing a part of an area A1 surrounded by a dashed-dotted line of the component 4-7 of an electronic device shown in FIG. 3. In this specification, a position of a solder joint is denoted on the basis of A, B, C, ... from the right to the left and 1, 2, 3, ... from the top to the bottom with the upper-right dummy bump as an original point in FIG. 5.

In accordance with a progression of temperature cycles ΔT, the strain range of the dummy bump 1 locating at the outermost expands firstly. Then, the strain range of the dummy bump 2 expands secondly and the strain range of the signal bump 3 expands lastly. This phenomenon is caused by decreases in stiffness of solder joints as cracks progress at the solder joints as a result of strain accumulation. Accordingly, the strain variation histories of the dummy bumps are preliminarily examined for calculating strain on the basis of information on temperature variations, thereby allowing it to calculate strain with considering the decreases in stiffness and to accurately predict a life of an electronic device.

Figure 7:
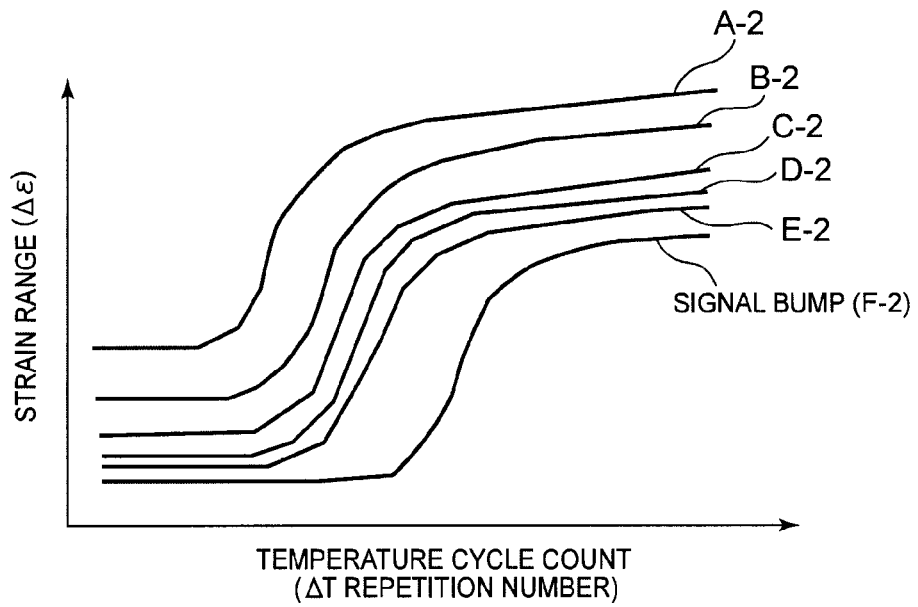
FIG. 7 is a conceptual graph showing relation between a temperature cycle number and a strain range.

FIG. 7 is a graph showing an example of strain variation histories of dummy bumps (A-2 to E-2) and the signal bump shown in FIG. 4 through a finite element method (FEM), i.e., a numerical analysis. In FIG. 4, it is observed that the strain variation becomes larger starting from the outer dummy bump. Accordingly, the result shows a tendency similar to FIG. 6.

Figure 8:
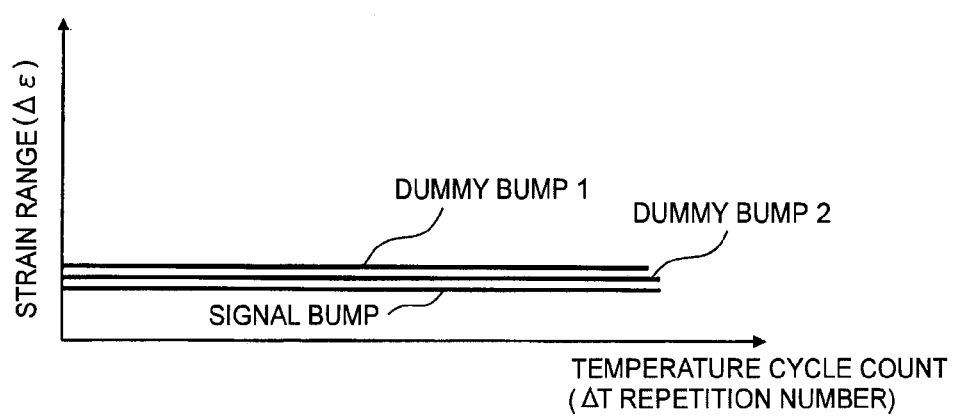
FIG. 8 shows a result of variation history of strain ranges obtained through FEM numerical analysis.

On the other hand, FIG. 8 is a view showing strain amplitude estimated with a traditional estimation method. The strain amplitude is determined regardless of a fracture and a progression of damage such as cracks at solder joints.

(Preparation of Database)

The first embodiment can be embodied on the basis of the above consideration as follows.

First, a database indicating a strain variation history is previously prepared to estimate each solder joint, of which life is to be predicted, for stiffness deceases with a progression of temperature cycle.

Figure 9:
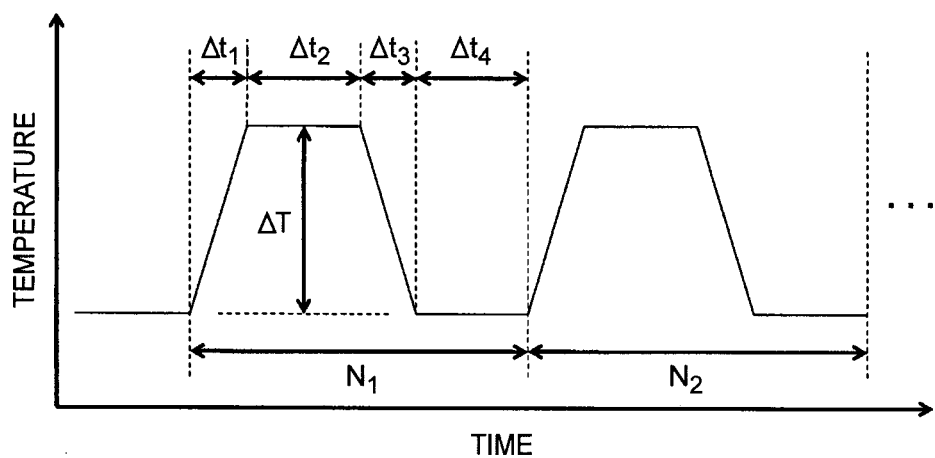
FIG. 9 is a conceptual graph showing a load state theoretically having constant temperature width and constant time.
Figure 10:
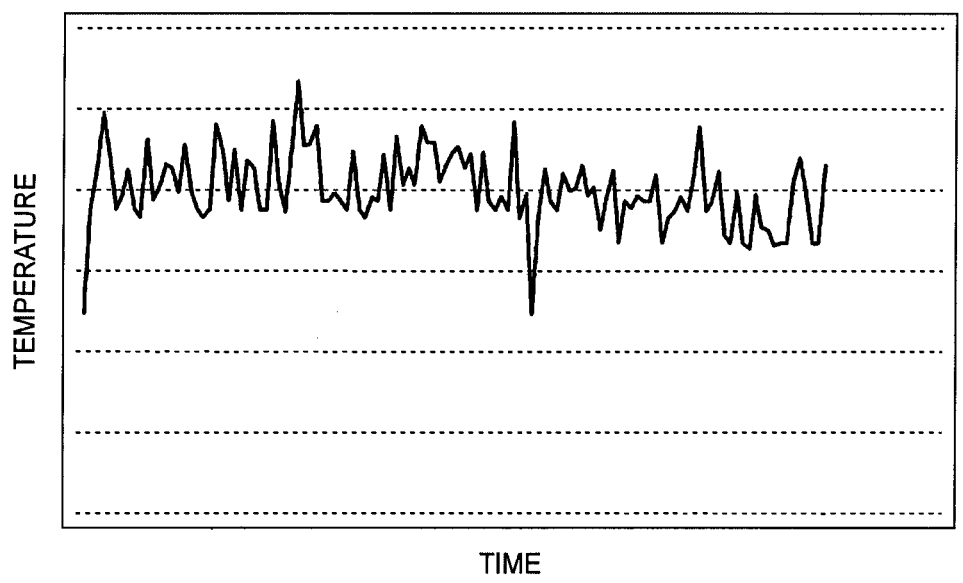
FIG. 10 is a conceptual graph showing actual temperature variation history.

Here, a method considering stiffness decreases of solder joints due to damage thereof is applied to a numerical analysis such as FEM, provided that a temperature cycle is repeated as shown in FIG. 9. The method provides a relation as shown in FIG. 6 between the temperature cycle number and the strain range Δε. The relation as shown in FIG. 6 varies depending on temperature amplitude (i.e., ΔT in FIG. 9), holding time (i.e., ΔT2 and ΔT4 in FIG. 9) and rise time and fall time (i.e., ΔT1 and ΔT3 in FIG. 9). Products on the market do not receive the cycle shown in FIG. 9 having constant temperature amplitude and constant time but receive a more complicated temperature cycle as shown in FIG. 10. Such a complicated temperature cycle requires a database to allow it to predict a correct strain range with considering the damage at the solder joints.

Figure 11:
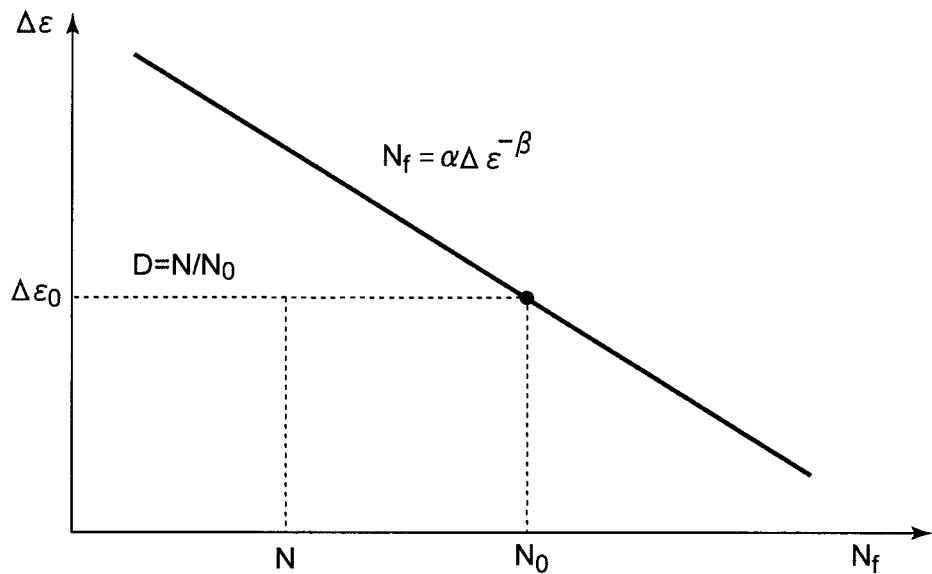
FIG. 11 is a conceptual view showing an exponential law until solder is fractured.

Then, a relation between the damage index and an increased amount of the strain range at each solder joint to require life prediction is utilized as information to be stored in the database. The damage index D is an index indicating a fatigue degree when applying different amplitude loads. The solder joint reaches the end of its life at the time when D equals to 1, thereby leading to a fracture. FIG. 11 is a graph to be utilized for a life predicting method when repeating amplitude in the constant strain range $\Delta\epsilon_0$. Repeating the amplitude in the constant strain range $\Delta\epsilon_0$ yields the repetition number $N_0$ from starting to the fracture. The number $N_0$ is derived from an exponential law (i.e., an exponential law called the Coffin-Manson's law or the Basquin's law particularly for a case of solder). Here, the denotation is as follows.

α, β: Constant determined for each material
Nf: Crack occurrence cycle
$N_0$: Crack occurrence cycle number on the assumption of repletion of strain $\Delta\epsilon_0$
N: Cycle number of actually loaded $\Delta\epsilon_0$
Δε: Strain range
D: Damage index after N cycle load Meanwhile, a life predicting method for two or more kinds of amplitude in different strain ranges (i.e., temperature ranges) is shown in FIG. 1 and FIGS. 12 to 14.

Figure 12:
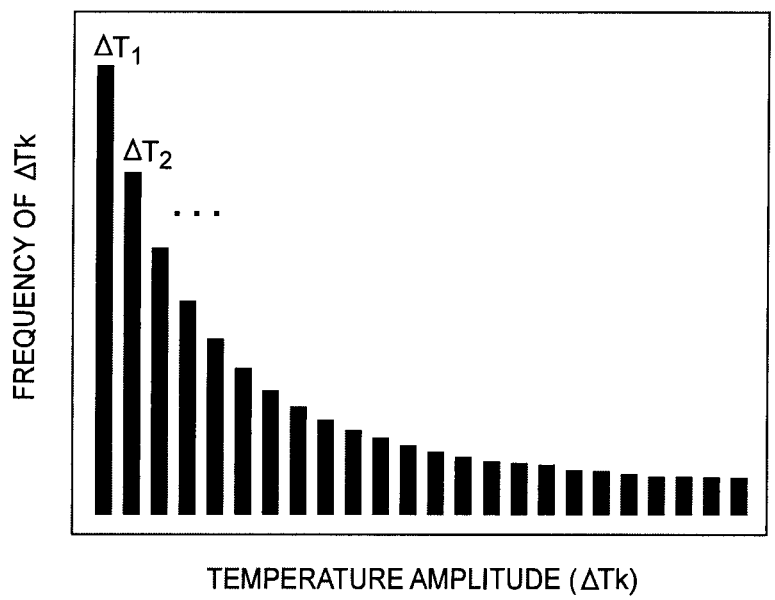
FIG. 12 is a conceptual graph showing relation between temperature amplitude and frequency thereof.

The temperature history data (see FIG. 10) is converted into the temperature amplitude data (i.e., Step S003 in FIG. 1) with a method so called "cycle count (also referred to as a cycle count method)." Further, the cycle number and cycle length of a temperature history are simultaneously examined. FIG. 12 is a graph showing an example of the temperature amplitude data. There is known a specific method of the CYCLE COUNT, for example, ASTM E 1049-85 "Standard practices for cycle counting in fatigue analysis", ASTM Standards, Vol. 03.01 (Reapproved 1997), Philadelphia, 1999.

Figure 13:
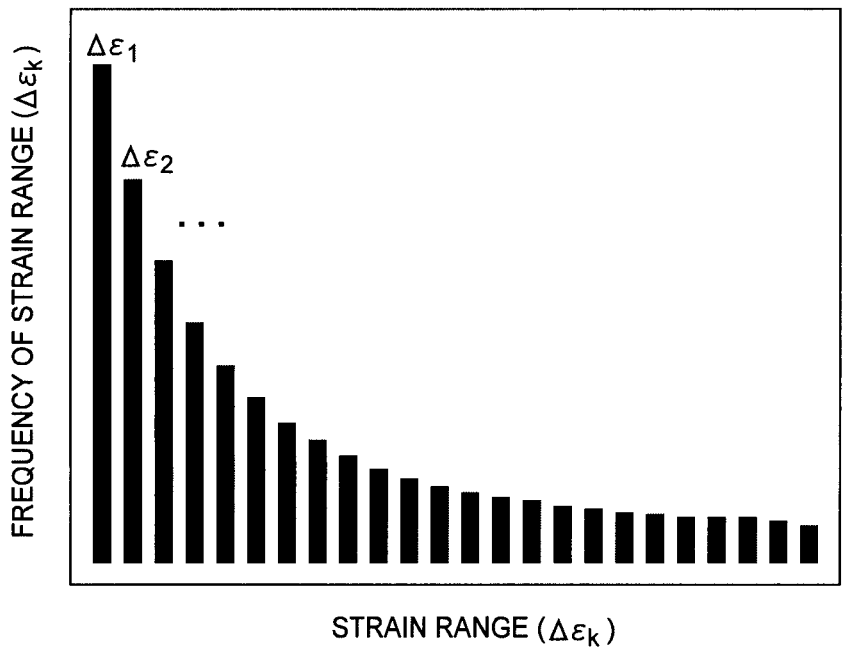
FIG. 13 is a conceptual graph showing relation between a strain range and frequency thereof.

Further, the temperature amplitude data are converted into the strain range to occur at the solder joint with reference to the previously prepared response surface (i.e., Step S004 in FIG. 1). FIG. 13 shows an example of the data converted into the strain range. Here, the response surface is an expression prepared through a numerical analysis assuming various temperature ranges and being capable of accurately predicting strain to occur at a solder joint. At preparing the response surface, each solder joint is assumed to have constant stiffness regardless of the cycle progression in order to eliminate complications without considering stiffness decreases due to damage progression at the solder joint. A life is derived from a summation D of the reciprocal of each fracture life $N_k$ to be derived from each strain range (see equation 1 and equation 2) in accordance with a linear cumulative damage law (also called a Miner's law) when applying amplitude in different strain ranges $\Delta\epsilon_k$.

[Equation 1]

$$N_k = \alpha \Delta\epsilon_k^{-\beta} \qquad \text{[Equation 1]}$$

[Equation 2]

$$D = \sum_k \frac{1}{N_k} = \sum_k \frac{1}{\alpha \Delta\epsilon_k^{-\beta}} \qquad \text{[Equation 2]}$$

Figure 14:
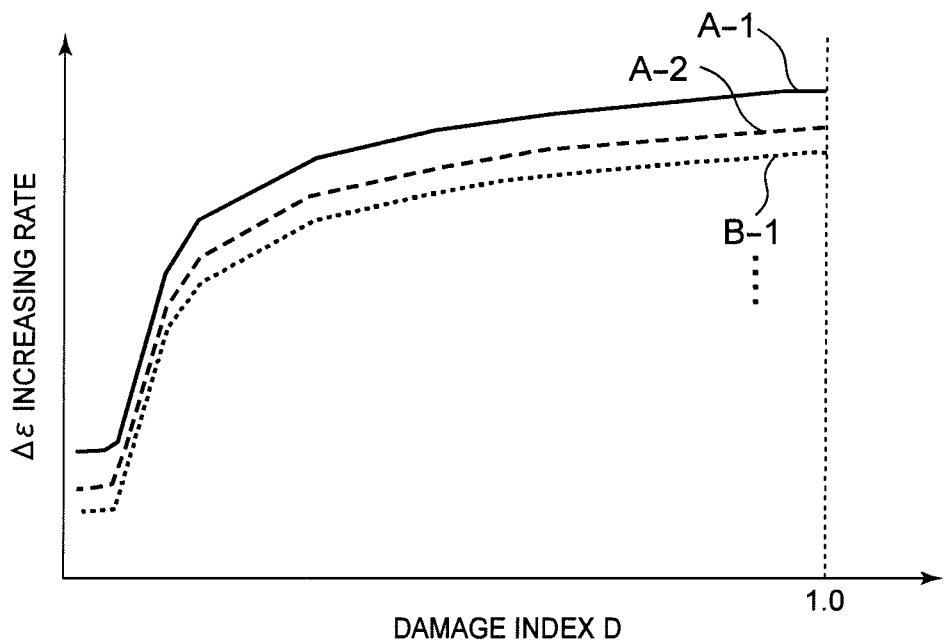
FIG. 14 is a graph showing relation between a damage index and a strain range increasing rate.

FIG. 14 is a graph showing relations between the damage index D denoted by the horizontal axis and an increasing rate of the strain range Δε denoted by the vertical axis at the three solder joints (i.e., A-1, A-2 and B-1 in FIG. 5). Here, the increasing rate of the strain range $\Delta\epsilon$ is an increasing rate of a strain range to occur owing to the application of the temperature amplitude same as that at a damage index of D with respect to an initial strain range $\Delta\epsilon_0$, provided that the initial strain range $\Delta\epsilon_0$ is defined as a strain range to occur at a solder joint owing to the application of temperature amplitude in an initial state before a damage progresses at the solder joint. Numerical analyses including FEM can provide the increasing rate of the strain range $\Delta\epsilon$. A specific analysis is recited in "Damage Path Simulation at Solder Bump Joints," Japan Society of Mechanical Engineers, Collection of Papers (Volume A), 73-736 (2007-12).

Figure 15:
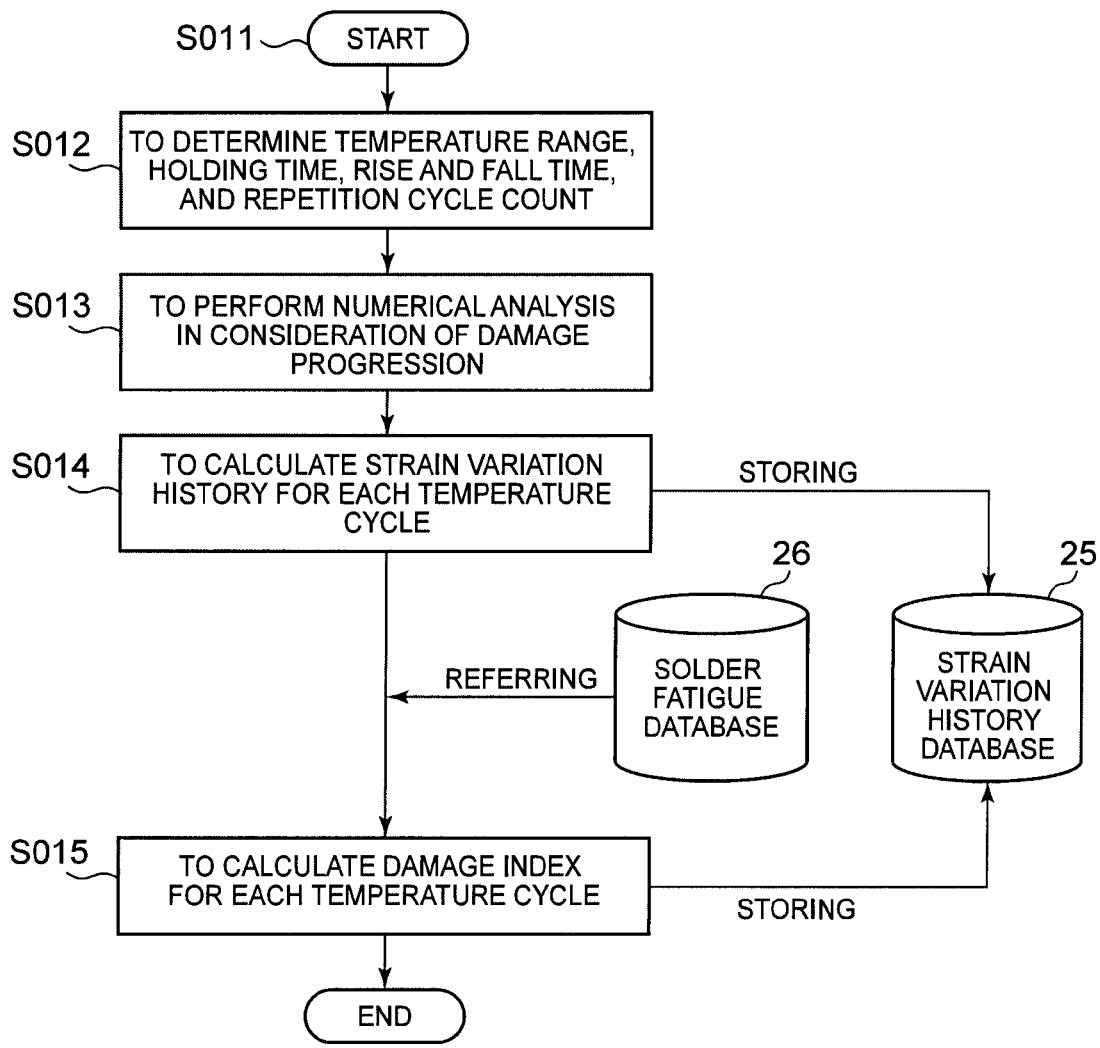
FIG. 15 is a flowchart of a preparation process of a strain variation history database.
Figure 16:
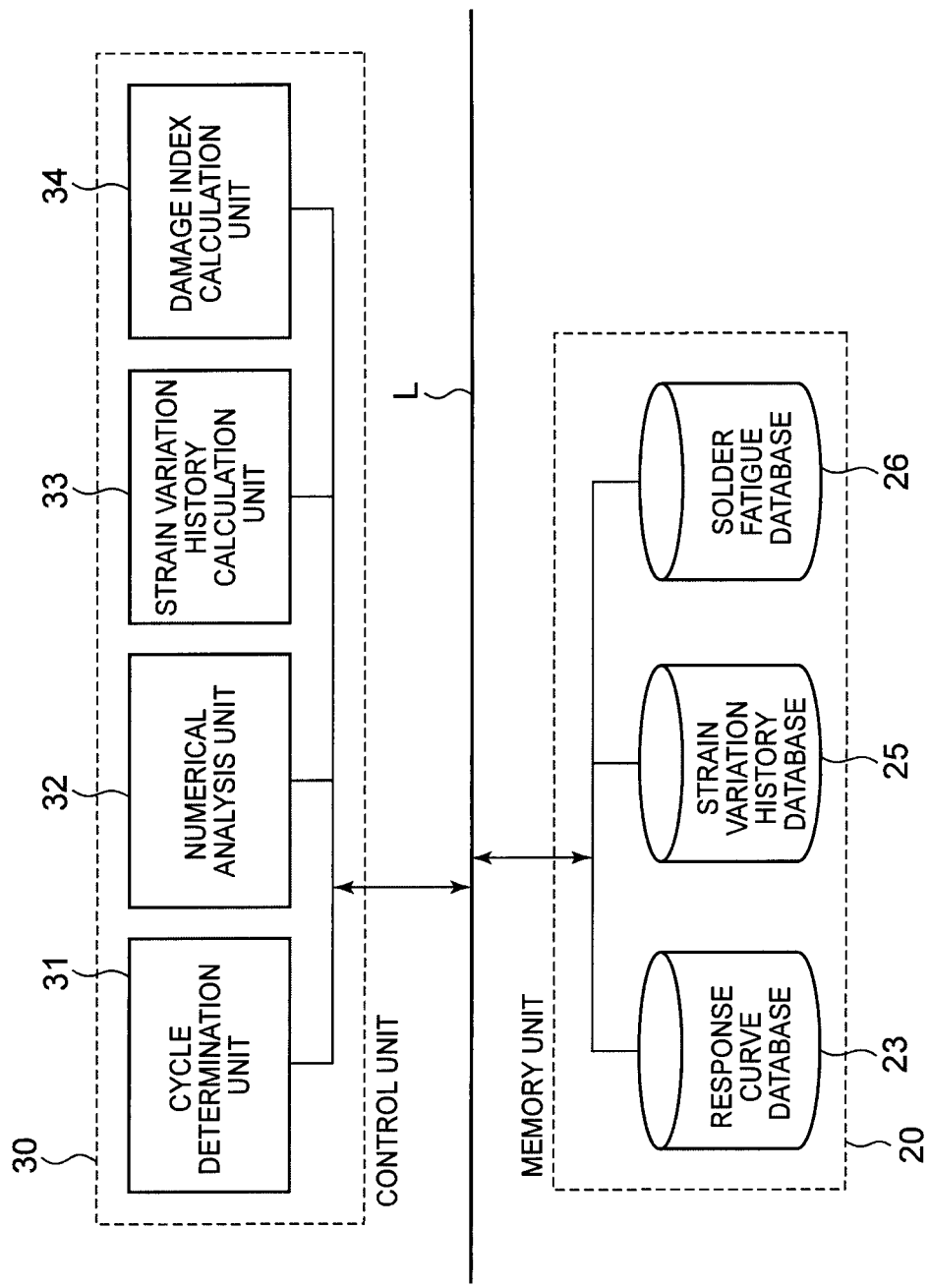
FIG. 16 is a block diagram of an apparatus to prepare the strain variation history database.

The above relations are previously stored in the strain variation history database 25 through a numerical analysis and the like, and then, the increasing rate of the strain range $\Delta\epsilon$ due to a damage progression can be obtained by checking the damage index D obtained from the temperature history under the usage conditions for products. FIGS. 15 and 16 are block diagrams showing a preparation process of the strain variation history database and an apparatus to prepare the strain variation history database, respectively.

(Preparation Process of Strain Variation History Database)
(Step S011 to Step S012)

An eleventh control unit (i.e., a cycle determination unit) 31 determines a temperature range, temperature holding time, temperature rise time, temperature fall time and the number of temperature cycle repetition.

(S013)

A twelfth control unit (i.e. a numerical analysis unit) 32 conducts a numerical analysis with considering a damage progression. Specifically, temperature conditions specified by FEM are set up, and then, a life-ended portion is deleted or stiffness thereof is extremely decreased at the time when the strain range occurring inside solder reaches the cycle number of fatigue life determined by the Coffin-Manson's law or the Basquin's law, thereby simulating cracks and estimating a damage progression. The details are recited in Vol. 73 (736) (2007-12), Collection of Papers (A), Japan Society of Mechanical Engineers.

(Step S014)

A thirteenth control unit (i.e. a strain variation history calculation unit) 33 calculates a strain variation history for each temperature cycle. Further, the strain variation history calculation unit 33 stores the strain variation history obtained for each temperature cycle in the fifth memory unit (i.e., the strain variation history database) 25.

(S015)

A fourteenth control unit (i.e., a damage index calculation unit) 34 calculates (i.e., estimates) the damage index D for each temperature cycle with reference to an eleventh memory unit (i.e., a solder fatigue database) 26. Further, the damage index calculation unit 34 stores the increasing rate of the strain range $\Delta\epsilon$ for each temperature cycle and the obtained damage index D corresponding thereto in the fifth memory unit (i.e., the strain variation history database) 25.

Alternatively, Step S015 may be executed taking an arbitrary opportunity, in real time, at given timing or the like. For example, Step S015 may be executed periodically or at the timing of ON or/and OFF of power as the given timing.

(Effect)

Here, the first benefit of using the damage index D in order to obtain an increased amount of the strain range $\Delta\epsilon$ is to obtain the strain range increasing rate $\Delta\epsilon$ with reference only to the damage index without considering a range, holding time and rise and fall time of an applied temperature. That is, the preparation process of strain variation history database is easy to apply to complicated temperature variation under real usage conditions which is not the same as a simple temperature variation like constant temperature amplitude. As the second benefit, there are no large variations in the relation between the damage index D and the increasing rate of the strain range $\Delta\epsilon$ to be caused by the range and holding time etc. of the applied temperature as a result of robustness of the relation.

According to the above benefits, the relation between the damage index and the strain range due to the typical temperature history are previously examined through a numerical analysis, thereby allowing it to obtain the strain-range increasing rate due to a variety of temperature history with ease and relatively high accuracy.

In order to predict the strain-range increasing rate more accurately, it is also possible to utilize a method to store two or more relations of FIG. 14 in the database through a numerical analysis having the temperature range, holding time, rise time and fall time as parameters and to apply a relational expression appropriate for the applied temperature range.

Here, in the first embodiment, a method to calculate a strain range has been described. The method examines the amplitude, cycle number, mean temperature and periodic length of temperature variations from temperature history information by means of the CYCLE COUNT to calculate the strain range on the basis of a response surface previously prepared. However, the first embodiment is not limited to the method. The strain range could be predicted even without all the physical quantities such as the temperature amplitude, the cycle number and the periodic length, depending on usage environment of an object to be checked. Specifically, only the amplitude and the cycle number allow it to predict the strain range in some cases.

Accordingly, it is possible to predict a life of a solder joint on the basis of the following two conditions:

(1) At least one of physical quantities such as the amplitude, cycle number, mean temperature and periodic length of temperature variations can be examined by means of cycle number from temperature history information; and (2) The strain range can be calculated on the basis of a response surface previously prepared for at least one of the physical quantities examined in (1).

(Modification of First Embodiment)

Figure 17:
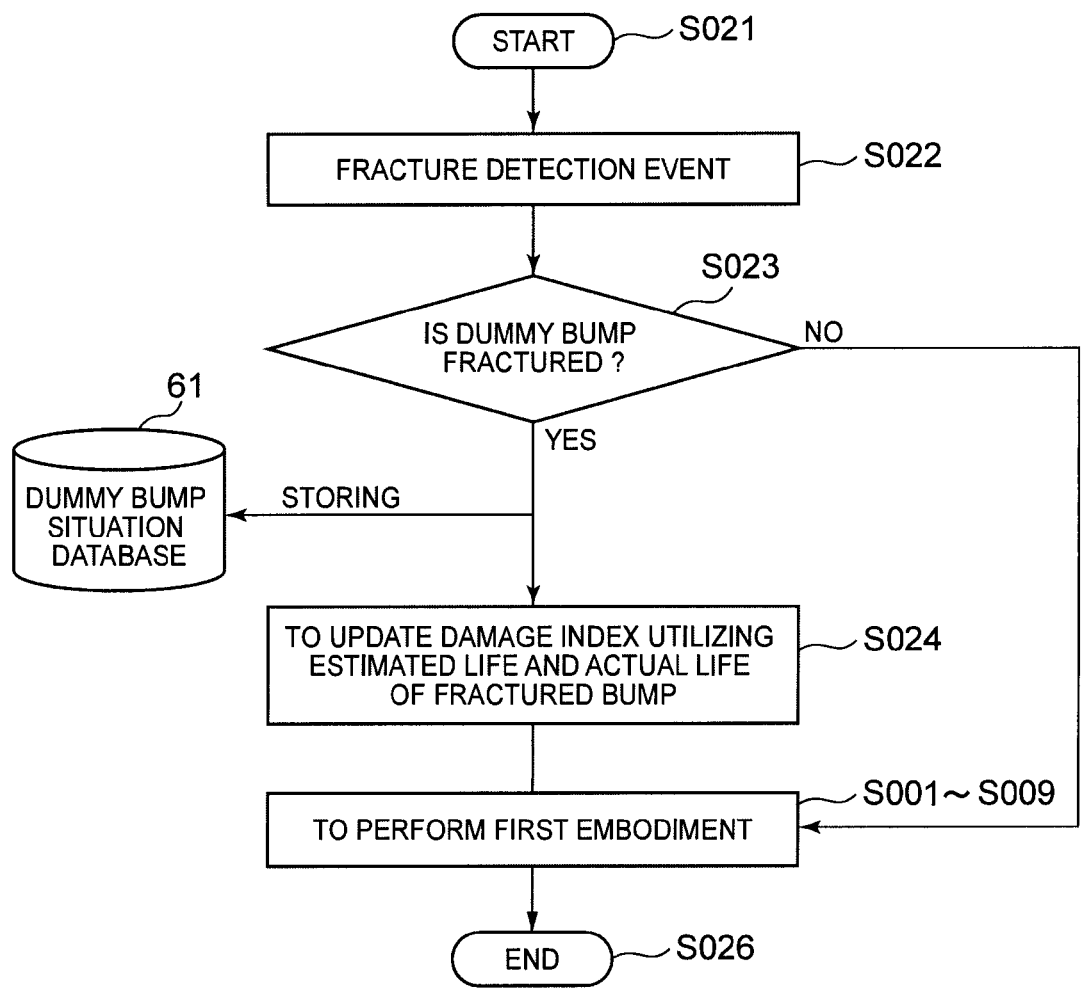
FIG. 17 is a flowchart of a process showing a modification of the first embodiment.
Figure 18:
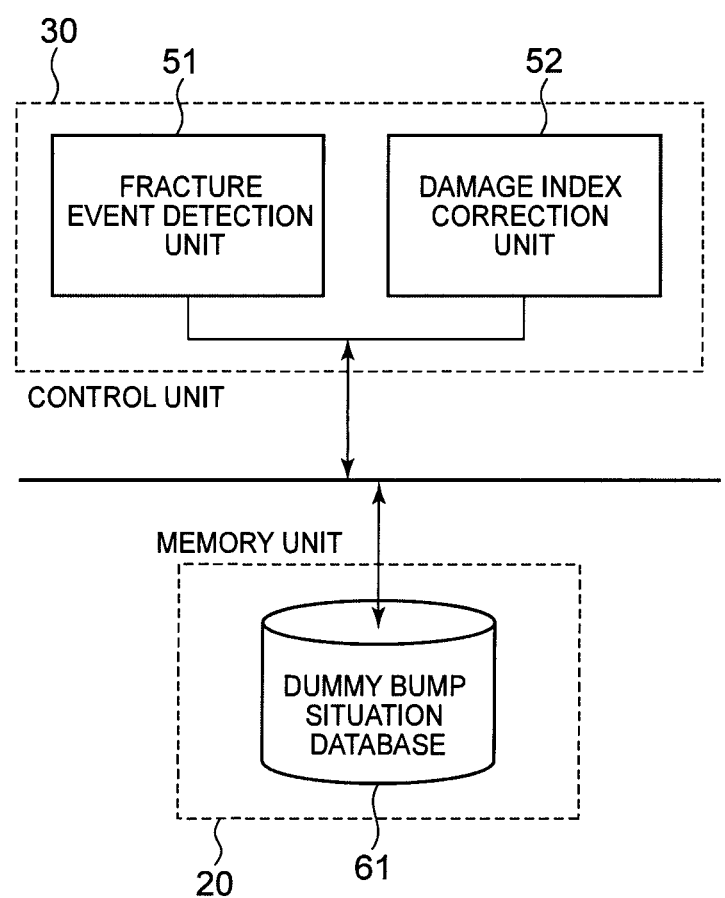
FIG. 18 is a block diagram of an apparatus to perform an error correction routine.

A modification of the first embodiment will be explained. The process of life prediction of the present modification is different from that of the first embodiment in a point that the modification is provided with a routine. The routine calculates an error between an estimated life and an actual life of a dummy bump to correct the error when a fracture of the dummy bump is detected. FIG. 17 shows a life predicting method having the routine of the error correction mounted. Further, FIG. 18 shows a structure added to the first embodiment of structures necessary for performing the life predicting method.

(Step S021 to Step S022)

A dummy bump fracture detection event is arranged before the life predicting method of the first embodiment (i.e. Step S025).

A twenty-first control unit 51 (i.e., a fracture event detection unit) determines whether or not the dummy bump fractures (Step S022). When the control unit 51 determines that the dummy bump does not fracture, the control unit 51 performes the method of the first embodiment (i.e., Step S001 to Step S009) is performed (see FIG. 1).

(Step S023)

When it is determined that the dummy bump fractures, a twenty-second control unit (i.e., a damage index correction unit) 52 reads the previously obtained damage index with reference to the damage index database 24. Then, the damage index correction unit 52 performs a comparison between the previously given damage index and the newly obtained damage index. Further, when a certain difference is definite between the damage indexes in the comparison result, the damage index correction unit 52 corrects a predicted life of a solder joint which has not fractured yet (Step S023).

Figure 19:
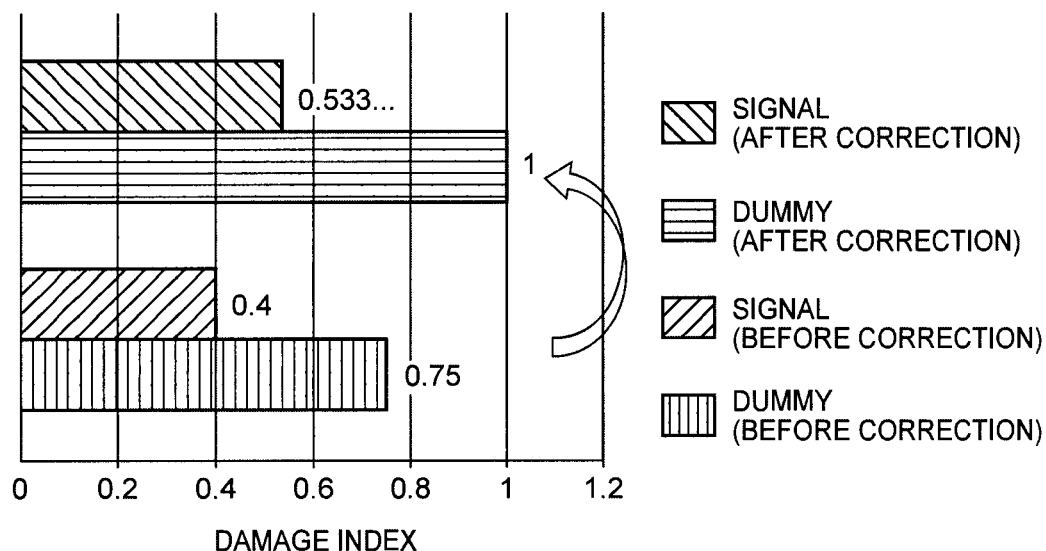
FIG. 19 shows an example of life estimation correction according to the modification of the first embodiment.

A correction method of the predicted life will be explained with reference to an example shown in FIG. 19. A fracture is supposed to occur when the damage index D reaches 1. Here, the fracture is assumed to be detected at the solder joint when D=0.75 as shown in FIG. 19. In this case, it is determined that the damage corresponding to $\Delta D=0.25$ ($=1-0.75$) has been applied for some unexpected reason. Accordingly, the damage index of a solder joint which has not yet fractured is divided by D=0.75. That is, a new damage index is to be 0.533 which is obtained by dividing a damage index of 0.4 by 0.75.

Further, the damage index correction unit 52 stores the corrected damage index 0.533 through the above calculation in a memory unit (i.e., a dummy bump situation database) 61. The fracture information and damage index of the solder joint stored in the memory unit (i.e., the dummy bump situation database) 61 are provided to a host side by utilizing media such as a self-monitoring, analysis and reporting technology (SMART) as needed. Subsequently, the process of the first embodiment (i.e., Step S001 to Step S009) is executed (see FIG. 1).

Second Embodiment

A second embodiment will be described with reference to FIGS. 2 and 3. The second embodiment relates to a life predicting apparatus for a solder joint.

Figure 3:
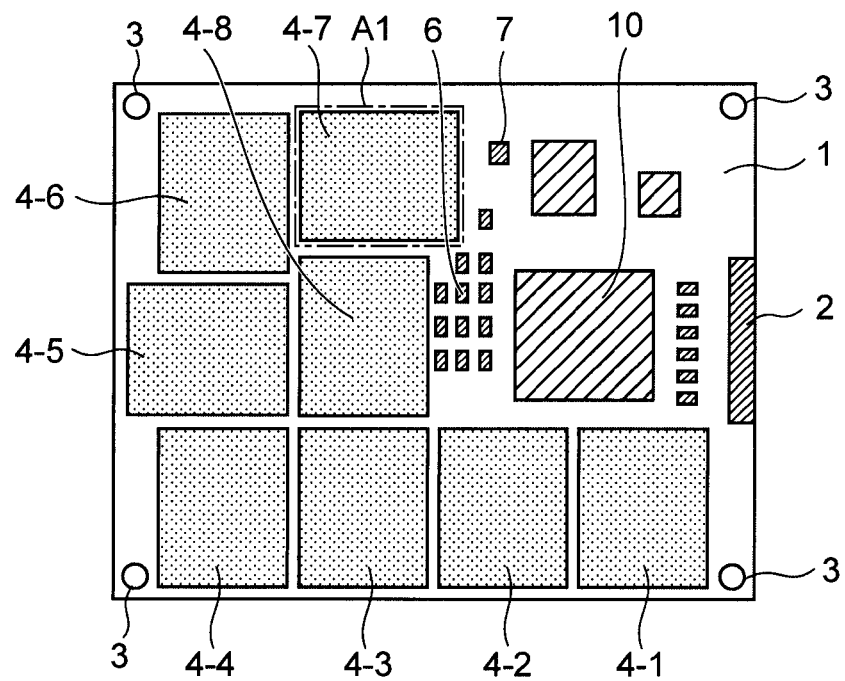
FIG. 3 is a schematic view showing a structure of the second embodiment.

FIG. 3 is a schematic view showing an example of the second embodiment having semiconductor memories 4-1 to 4-8, a capacitor 6, a detection unit 7 and a control unit 10 mounted on the mounting board 1. The semiconductor memories 4-1 to 4-8 are connected to the mounting board 1 via solder joints and the like. The detection unit 7 measures electric characteristics of the respective joints of the semiconductor memories 4-1 to 4-8 and observes connection states thereof. Further, the detection unit 7 measures a temperature of the mounting board 1. A part of the semiconductor memory can be used as the memory unit 20.

Figure 2:
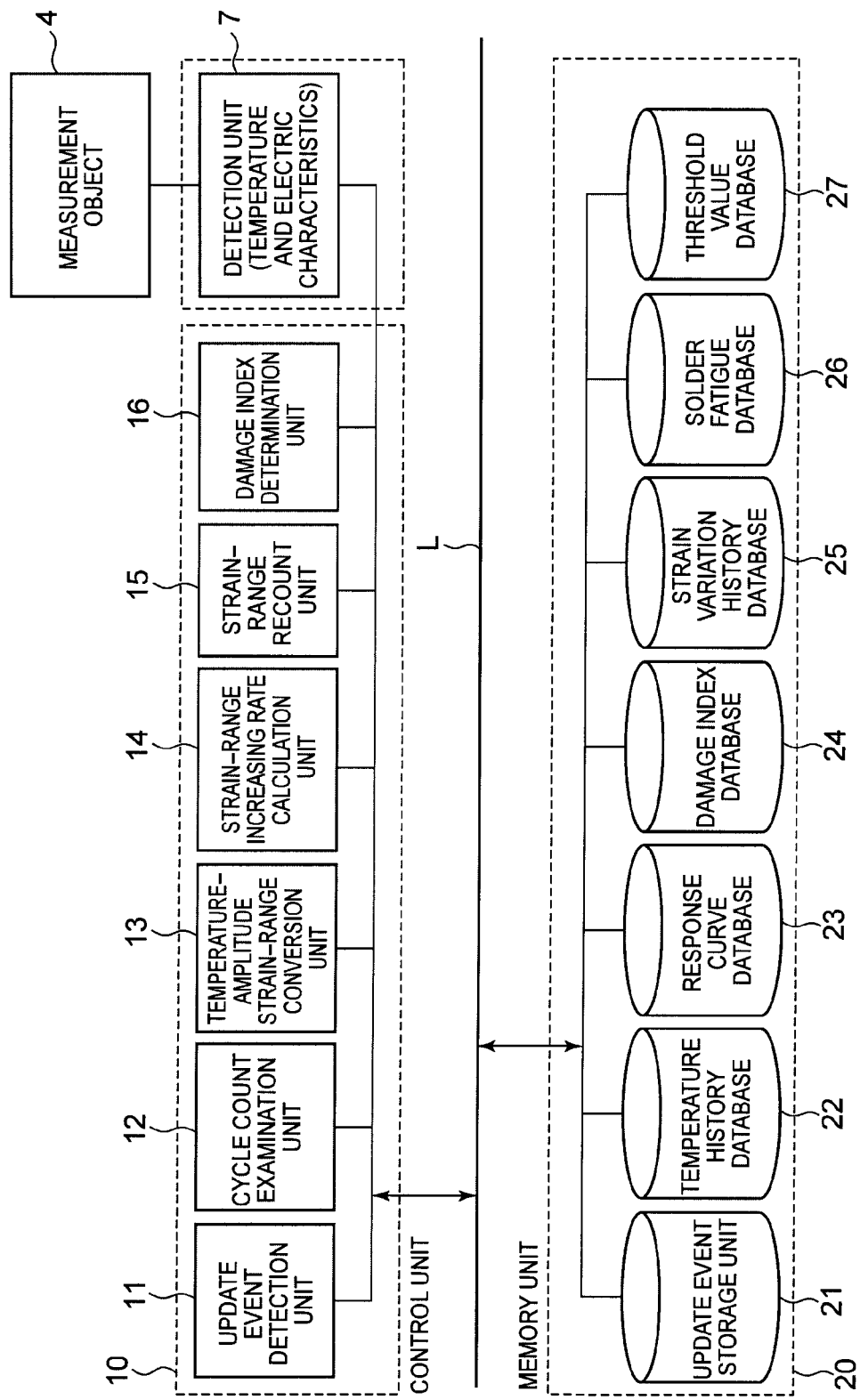
FIG. 2 is a block diagram according to a second embodiment.

FIG. 2 is a block diagram according to the second embodiment. The second embodiment includes the detection unit 7, the control unit 10 and the memory unit 20 as components. These are mutually connected via a signal line L through which information and signals are exchanged. The signal line may adopt a wired form, a wireless form or a mixed form thereof.

Corresponding to the first embodiment, the control unit 10 is provided with the update event detection unit 11, the cycle number examination unit 12, the temperature-amplitude/strain-range conversion unit 13, the strain-range increasing rate calculation unit 14, the strain-range recount unit 15 and the damage index determination unit 16. The memory unit 20 is provided with the update event storage unit 21, the temperature history database 22, the response surface database 23, the damage index database 24, the strain variation history database 25, the solder fatigue database 26, and the threshold value database 27.

Corresponding to the modification of the first embodiment, the control unit 10 may be further provided with the fracture event detection unit 31 and the damage index correction unit 32 and the memory unit 20 may be further provided with a dummy-bump state database 61.

A CPU is utilized as the control unit 10, for example. Further, a semiconductor memory may be utilized for the memory unit 20. However, not being limited to the above, the memory unit is only required to be a recording medium capable of storing information and programs. Accordingly, an LSI such as a NAND type semiconductor memory, an HDD or a ROM may be utilized therefor.

The detection unit 7 (i.e., the fracture event detection unit 51) may be provided with a circuit to measure a resistance value of the solder joint 71, a circuit to measure impedance or/and the like, for example. The detection unit 7 can detect a fracture by measuring electric characteristics of a solder joint. For example, it is possible to detect subsidiary fracture by detecting rapid increase of electric resistance caused by the fracture of the joint. Further, the detection unit 7 may be provided with a thermocouple for measuring temperatures. When the circuit to measure impedance is an analog circuit and the output of the thermocouple is an analog signal, the detection unit 7 may include an A/D converter. Conversion from analog signals to digital signals enables the control unit 10 and the memory unit 20 to easily deal with these signals.

Operation, function and effects of the second embodiment will not be repeated as described in the first embodiment and the modification thereof.

Third Embodiment

Next, a third embodiment will be explained below with reference to FIG. 20. The third embodiment includes characteristics to form a signal line for detecting a fracture.

Figure 20:
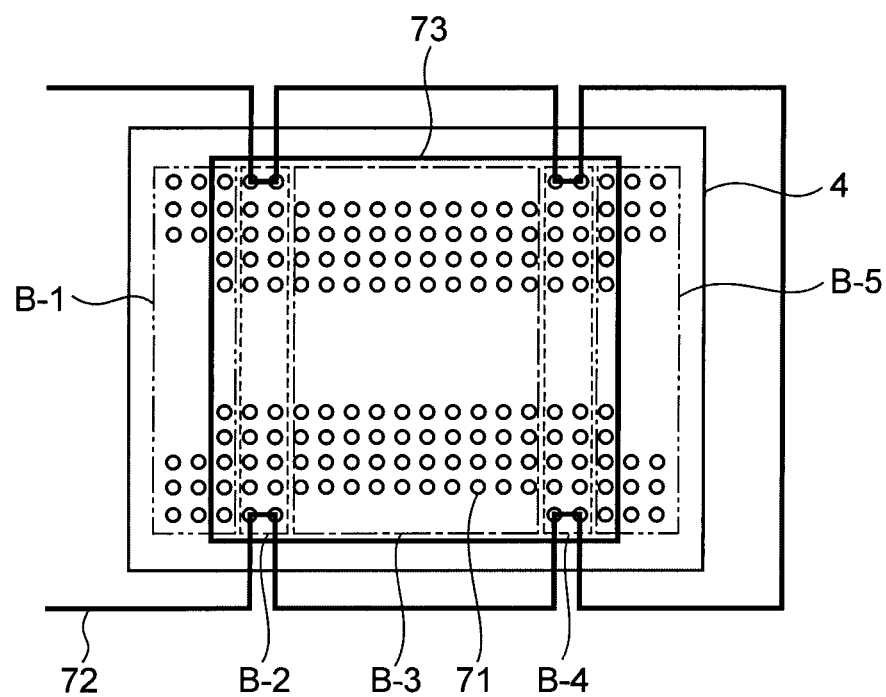
FIG. 20 is a schematic view showing a structure of a third embodiment.

As shown in FIG. 20, two or more solder joints 71 are arranged in a rectangular semiconductor memory 4. A silicone chip 73 included in the semiconductor memory 4 is slightly smaller than the outermost circumference of the semiconductor memory 4 and is formed inside the semiconductor memory 4.

The solder joints 71 are arranged in a dummy bump area (i.e., a second joint B-1), a fracture detection area (i.e., a third joint B-2), a signal line area (i.e., a first joint B-3), a fracture detection area (i.e., a third joint B-4) and a dummy bump area (i.e., a second joint B-5) which are formed in this order in the direction of a line-symmetric axis of the rectangular semiconductor memory 4. That is, the fracture detection area is formed between the signal line area and the dummy bump area.

The respective dummy bump areas (B-1, B-5) are surrounded by a double-dotted line in FIG. 20. The dummy bumps in the areas mechanically connect the semiconductor memory and the mounting board 1 to each other, but do not relay the semiconductor memory and the mounting board 1 electrically.

The signal line area (B-3) is surrounded by a dash-dotted line in FIG. 20. The solder joints in this area provide not only a mechanical connection between the semiconductor memory 4 as an electric device and the mounting board 1, but also an electrical connection therebetween.

The respective fracture detection areas (B-2, B-4) are surrounded by a dashed line in FIG. 20. The solder joints in the areas provide the mechanical connection between the semiconductor memory 4 as an electric device and the mounting board 1 but do not provide the electrical connection therebetween. Here, a signal line 72 for detecting a fracture is formed by utilizing a part of the solder joints in the areas. The signal line 72 is connected to the detection unit 7 to be capable of monitoring the connection state between the semiconductor memory 4 and the mounting board 1. In the example shown in FIG. 20, when pairing two solder joints adjacent to each other at the outermost of the fracture detection area, four pairs of joints to mutually face are connected serially with one line. In some cases, only one pair of joints or only two pairs thereof occupying contrapositive locations on the rectangular semiconductor memory 4 may be connected. At this time, choosing the pairs of the joints having the most drastic change in the temperature enables it to detect the fracture of solder joints at an early stage.

Arranging the fracture detection area between the dummy bump area and the signal line area as described above enables it to use the fracture detection area having less influence of its variations on the life prediction than the dummy bump area and to accurately predict the life. The dummy bump area in the vicinity of the outer circumference is to fracture earlier than the fracture detection area or the signal line area. This can be physically understood in terms of the fact that solder joints receive more mechanical load toward the outer side of a package and all the inner joints averagely receive any loads other than the load received by the outer joints. Strain ranges of the respective inner solder joints are more averaged than those of the outer solder joints. The respective inner solder joints receive an equivalent load averaged over the inner solder joints. As a result, variations in the life are reduced. The tendency of the variations is proved with a load test such as a temperature cycle test.

Fewer variations in the characteristics of the fracture detection area are beneficial to the damage index correction of the signal bump performed at Step 023 of the first embodiment. The solder joints for the fracture detection having fewer variations allow the other solder joints for the damage index correction to have fewer variations, thereby enabling it to accurately predict the life. The fracture detection is performed preferably at the dummy bump area in the outer side of the package to value an early detection while the fracture detection is performed preferably at the solder joints in the inner side of the dummy bump area to enable an accurate prediction. Appropriately selecting a solder connection portion for fracture detection enables it to keep balance between early detection and an accurate life prediction.

(Modification of Third Embodiment)

Figure 21:
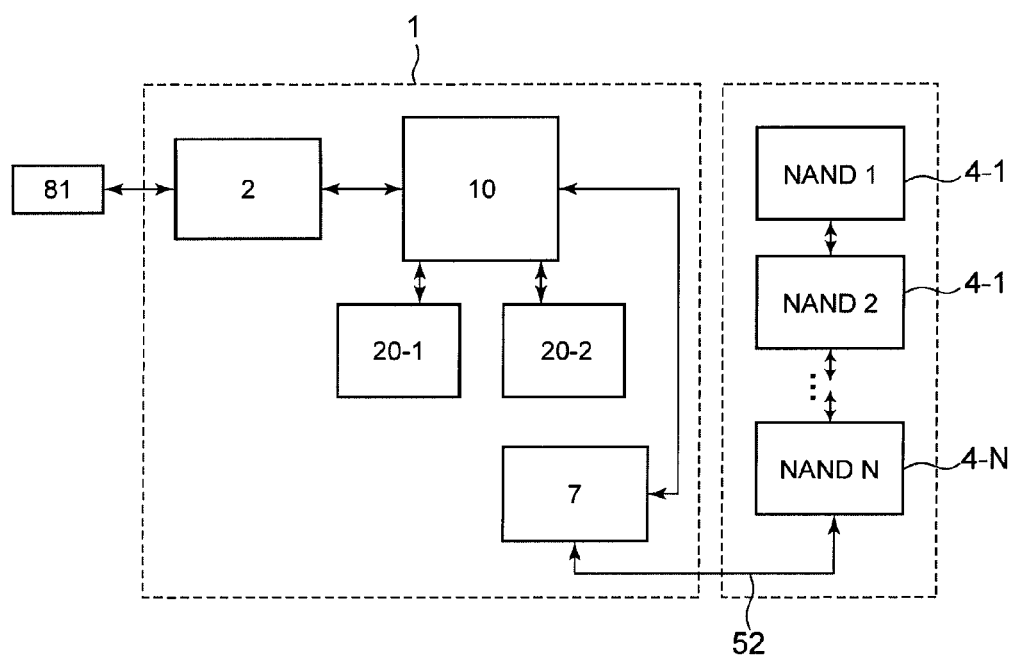
FIG. 21 is a schematic view showing a modification of the third embodiment.

A modification of the third embodiment combines the first and second embodiments with a chain for fracture detection to enable it to appropriately predict a life. FIG. 21 shows the modification of the third embodiment.

Each semiconductor memory (4-1, 4-2, ... , 4-N) in FIG. 21 is connected to the detection unit 7 in a traversable manner with the fracture detection signal line 72. Accordingly, solder joints of two or more semiconductor memories 4 can be monitored with the detection unit 7 locating at one point.

At least any one of the above-described embodiments can prepare a test schedule to enable it to efficiently execute test items considering loads to be applied by diagnostic itself to devices.

While a certain embodiment of the invention has been described, the embodiment has been presented by way of examples only, and is not intended to limit the scope of the inventions. Indeed, the novel elements and apparatuses described herein may be embodied in a variety of other forms; furthermore, various omissions, substitutions and changes in the form of the methods described herein may be made without departing from the spirit of the invention. The accompanying claims and their equivalents are intended to cover such forms or modifications as would fall within the scope and spirit of the invention.

What is claimed is:

1. A life predicting method for a solder joint comprising:
referring to a temperature history of a measurement object having a solder joint;
examining at least one physical quantity selected from the group consisting of amplitude, a cycle number, a mean temperature, and a periodic length of a temperature variation with a cycle count method from the temperature history;
calculating a strain range by utilizing a previously prepared response surface from the physical quantity examined with the cycle count method; and
calculating a strain range increasing rate from the strain range with reference to a previously obtained damage index and a strain variation history of the strain range.

2. The method according to claim 1, further comprising
obtaining a new damage index with considering the strain range increasing rate which is calculated in the calculating step.

3. The method according to claim 2, further comprising
storing the new damage index in a database.

4. The method according to claim 2, further comprising
taking a predetermined action when the new damage index is equal to a predetermined threshold value or larger.

5. The method according to claim 2, further comprising:
performing a comparison between a previously given damage index at the time of a fracture and the new damage index when at least a part of the solder joint fractures; and
correcting a life prediction value of a solder joint having not yet fractured on the basis of the new damage index when a difference is detected in the comparison.

6. The method according to claim 1, wherein
the solder joint has an array-shaped joint structure.

7. The life predicting method according to claim 1, further comprising:
storing a relation between a strain variation history of the solder joint and damage of the solder joint in a database, the strain variation history being obtained through a previous numerical analysis; and
predicting the strain variation history of the solder joint from information stored in the database and a load of the measurement object, the load being measured under an usage condition.

8. A life predicting apparatus for a solder joint comprising:
a first memory to store a temperature history of a measurement object having a solder joint;
a second memory to store a response surface for obtaining a strain range from at least one physical quantity of amplitude, a cycle number, a mean temperature, and a periodic length of temperature variations;
a third memory to store a history of a damage index;
a fourth memory to store strain variations for obtaining a strain range increasing rate from a damage index;
a first control unit to obtain the temperature history with reference to the first memory unit;
a second control unit to examine at least one physical quantity selected from the group consisting of amplitude, a cycle number, a mean temperature, and a periodic length of temperature variations with a cycle count method from the history information of temperature;
a third control unit to calculate a strain range from the physical quantity examined with a cycle count with reference to the second memory unit; and
a fourth control unit to calculate the strain range increasing rate from the strain range calculated by the third control unit with reference to the third memory unit and the fourth memory unit.

9. An electronic device comprising:
   an electronic component;
   a mounting board;
   a first joint to mechanically connect the electronic component and the mounting board and to mediate an exchange of an electric signal between the electronic component and the mounting board;
   a second joint to mechanically connect the electronic component and the mounting board and not to mediate the exchange of the electric signal between the electronic component and the mounting board; and
   a third joint formed between the first joint and the second joint to mechanically connect the electronic component and the mounting board and to monitor a connection state between the electronic component and the mounting board.

10. The device according to claim 9 comprising the life predicting apparatus according to claim 8.

* * * * *